(12) United States Patent
Ayinde et al.

(10) Patent No.: US 11,636,593 B2
(45) Date of Patent: Apr. 25, 2023

(54) ROBUST SEGMENTATION THROUGH HIGH-LEVEL IMAGE UNDERSTANDING

(71) Applicant: EchoNous, Inc., Redmond, WA (US)

(72) Inventors: Babajide Ayinde, Redmond, WA (US); Fan Zhang, Bellevue, WA (US)

(73) Assignee: ECHONOUS, INC., Redmond, WA (US)

( * ) Notice: Subject to any disclaimer, the term of this patent is extended or adjusted under 35 U.S.C. 154(b) by 253 days.

(21) Appl. No.: 17/091,263

(22) Filed: Nov. 6, 2020

(65) Prior Publication Data
US 2022/0148158 A1 May 12, 2022

(51) Int. Cl.
*G06T 7/00* (2017.01)
*A61B 8/14* (2006.01)
(Continued)

(52) U.S. Cl.
CPC ............ *G06T 7/0012* (2013.01); *A61B 8/08* (2013.01); *A61B 8/14* (2013.01); *A61B 8/461* (2013.01); *G06N 3/02* (2013.01); *G06N 7/005* (2013.01); *G06T 2207/10132* (2013.01); *G06T 2207/20076* (2013.01); *G06T 2207/20081* (2013.01); *G06T 2207/20084* (2013.01)

(58) Field of Classification Search
None
See application file for complete search history.

(56) References Cited

U.S. PATENT DOCUMENTS 10,430,946 B1 * 10/2019 Zhou .................. A61B 5/02007
10,631,828 B1 4/2020 Hare, II et al.
(Continued)

FOREIGN PATENT DOCUMENTS

EP 3536245 A1 9/2019
WO WO 2018026431 A1 2/2018
(Continued)

OTHER PUBLICATIONS

International Search Report and Written Opinion, dated Feb. 24, 2022, for International Application No. PCT/US2021/058037, (11 pages).

(Continued)

*Primary Examiner* — Nancy Bitar
(74) *Attorney, Agent, or Firm* — Seed IP Law Group (57) ABSTRACT

A facility identifies anatomical objects visualized by a medical imaging image. The facility applies two machine learning models to the image: a first trained to predict a view probability vector that, for each of a list of views, attributes a probability that the image was captured from the view, and a second trained to predict an object probability vector that, for each of a list of anatomical objects, attributes a probability that the object is visualized by the image. For each object, the facility: (1) accesses a list of views in which the object is permitted; (2) multiplies the predicted probability that the object is visualized by the image by the sum of the predicted probabilities that the accessed image was captured from views in which the object is permitted; and (3) where the resulting probability exceeds a threshold, determines that the object is visualized by the accessed image.

18 Claims, 9 Drawing Sheets
(2 of 9 Drawing Sheet(s) Filed in Color)

(51) Int. Cl.
*A61B 8/00* (2006.01)
*A61B 8/08* (2006.01)
*G06N 7/00* (2006.01)
*G06N 3/02* (2006.01)

(56) References Cited

U.S. PATENT DOCUMENTS

| | | | |
|---|---|---|---|
| 2017/0360403 | A1 | 12/2017 | Rothberg et al. |
| 2018/0259608 | A1 | 9/2018 | Golden et al. |
| 2019/0140596 | A1 | 5/2019 | Shimamoto et al. |
| 2020/0054306 | A1 | 2/2020 | Mehanian et al. |
| 2020/0260062 | A1 | 8/2020 | Sharma et al. |
| 2021/0345992 | A1* | 11/2021 | Cook .................... G16H 50/20 |
| 2021/0350529 | A1 | 11/2021 | Ayinde et al. |

FOREIGN PATENT DOCUMENTS

| | | | |
|---|---|---|---|
| WO | WO 2018140596 A2 | | 8/2018 |
| WO | WO2020-020809 | * | 7/2019 |
| WO | WO 2019201726 A1 | | 10/2019 |
| WO | WO 2020020809 A1 | | 1/2020 |

OTHER PUBLICATIONS

Gal, Y., et al., "Dropout as a Bayesian Approximation: Representing Model Uncertainty in Deep Learning," Proceedings of the 33rd International Conference on Machine Learning, New York, NY, 2016, retrieved from arXiv:1506.02142v6, 12 pages.

Geifman, Y., et al., "Selective Classification for Deep Neural Networks," Jun. 2, 2017, retrieved from arXiv:1705.08500v2, 12 pages.

International Search Report and Written Opinion, dated Aug. 25, 2021, for International Application No. PCT/US2021/031415, 10 pages.

International Search Report and Written Opinion, dated Oct. 12, 2021, for International Application No. PCT/US2021/031193, 9 pages.

Lakshminarayanan, B., et al., "Simple and Scalable Predictive Uncertainty Estimation Using Deep Ensembles," 31st Conference on Neural Information Processing Systems (NIPS 2017), Long Beach, CA, retrieved from arXiv:1612.01474v3, 15 pages.

Liu, S. et al., "Deep learning in Medical Ultrasound Analysis: A Review," (2019). Engineering, 5(2): 261-275.

Redmon et al., "YOLOv3: An Incremental Improvement," Apr. 8, 2018, retrieved from arxiv.org/abs/1804.02767, 6 pages.

* cited by examiner

FIG. 8 permissible object table 800

| view | liver | kidney | diaphragm | spleen | heart | inferior vena cava | bladder | uterus | prostate |
|---|---|---|---|---|---|---|---|---|---|
| right-upper quadrant | 1 | 1 | 1 | | | | | | |
| left-upper quadrant | | 1 | 1 | 1 | | | | | |
| subcostal | 1 | | | | 1 | | | | |
| inferior vena cava | 1 | | | | | 1 | | | |
| suprapubic | | | | | | | 1 | 1 | 1 |
| others | | | | | | | | | |

810 — view
801 — right-upper quadrant
802 — left-upper quadrant
803 — subcostal
804 — inferior vena cava
805 — suprapubic
806 — others
811 — liver
812 — kidney
813 — diaphragm
814 — spleen
815 — heart
816 — inferior vena cava
817 — bladder
818 — uterus
819 — prostate

FIG. 9

ROBUST SEGMENTATION THROUGH HIGH-LEVEL IMAGE UNDERSTANDING

BACKGROUND

Ultrasound imaging is a useful medical imaging modality. For example, internal structures of a patient's body may be imaged before, during or after a therapeutic intervention. A healthcare professional typically holds a portable ultrasound probe, sometimes called a "transducer," in proximity to the patient and moves the transducer as appropriate to visualize one or more target structures in a region of interest in the patient. A transducer may be placed on the surface of the body or, in some procedures, a transducer is inserted inside the patient's body. The healthcare professional coordinates the movement of the transducer so as to obtain a desired representation on a screen, such as a two-dimensional cross-section of a three-dimensional volume.

Particular views of an organ or other tissue or body feature (such as fluids, bones, joints or the like) can be clinically significant. Such views may be prescribed by clinical standards as views that should be captured by the ultrasound operator, depending on the target organ, diagnostic purpose or the like.

In some ultrasound images, it is useful to identify anatomical structures visualized in the image. For example, in an ultrasound image view showing a particular region of the body, it can be useful to identify the shown organs and/or constituent structures within an organ. As one example, a right-upper quadrant view may show portions of the liver, kidney, and diaphragm organs.

Existing software solutions have sought to automatically identify organs or other anatomical structures in ultrasound images. These existing solutions seek to "detect" structures by specifying a bounding box in which each is visible, or "segment" structures by tracing each structure's boundaries in the image, for example.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

The inventors have recognized that conventional approaches to automatically identifying anatomical objects shown in ultrasound images have significant disadvantages. In particular, these conventional approaches frequently produce inaccurate results. While tuning a confidence threshold can sometimes exchange a high false positive rate with a high false negative rate, total error is often unacceptably high.

In response to recognizing these disadvantages, the inventors have conceived and reduced to practice a software and/or hardware facility that automatically identifies organs, sub-organ structures, or other anatomical objects in medical images such as ultrasound images in a way that leverages machine learning predictions about a particular view in which each image is captured and the objects that are visualized ("the facility"). By doing so, the facility provides an efficient way to control the appearance of objects in the image, because the object vector directly estimates the probability of occurrence of objects and the view vector directly estimates the probability of views. These two auxiliary probability output vectors are correlated, and can be used to generate an even more robust estimation of object occurrence likelihood using an Object Refining Module based on their relationship. Thus, the facility minimizes the false-positive predicted masks without compromising much false-negative rate.

In some embodiments, the facility applies to images, such as frames of an ultrasound video, a machine learning model trained to predict three characteristics of the image: (1) a view probability vector that indicates, for each of a number of possible views, the likelihood that the image was captured from the view; (2) an object probability vector that indicates, for each of a number of possible objects, the likelihood that the image visualizes the object; and (3) a set, or "cube," of segmentation masks that, for each pixel of the image, for each of the possible objects, indicate the probability that the pixel is part of a visualization of the object. In some embodiments, the facility averages or otherwise aggregates these predicted characteristics across a certain number of the most recent frames, such as 30.

For each possible object, in order to determine a probability that the object is visualized, the facility consults a list of the views in which the object is permissible to identify; sums the probabilities for those views contained by the view probability vector; and multiplies that some by the probability for that object contained by the object probability vector.

In some embodiments, the facility uses the determined object probabilities to select segmentation masks to use to augment the image with the shapes and locations of objects visualized therein. In some embodiments, the facility selects segmentation masks for objects whose determined object probabilities exceed an object probability threshold. In various embodiments, the facility uses the determined object probabilities and or selected segmentation masks in a variety of other ways.

By operating in some or all of the ways described above, the facility automatically identifies anatomical structures in medical images with greater accuracy than is conventionally possible.

Additionally, the facility improves the functioning of computer or other hardware, such as by reducing the dynamic display area, processing, storage, and/or data transmission resources needed to perform a certain task, thereby enabling the task to be permitted by less capable, capacious, and/or expensive hardware devices, and/or be performed with lesser latency, and/or preserving more of the conserved resources for use in performing other tasks. For example, by maximizing the usability of an initial medical image by more frequently identifying all structures visualized therein with significantly fewer false positives, the facility avoids many cases in which re-imaging is required. By reducing the need to reimage, the facility consumes, overall, less memory and processing resources to capture additional images and perform additional rounds of automatic structure identification.

Figure 1:
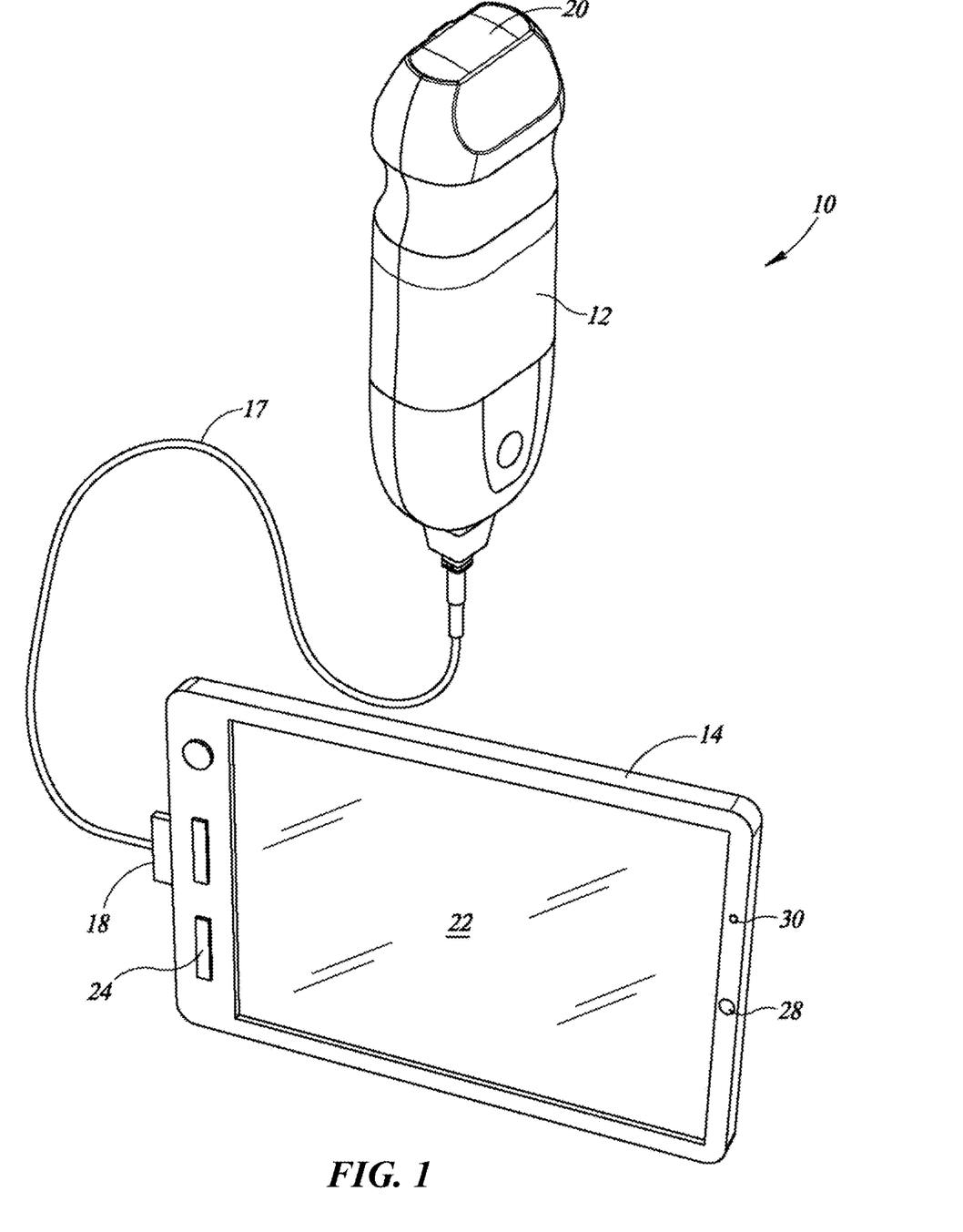
FIG. 1 is a schematic illustration of a physiological sensing device.

FIG. 1 is a schematic illustration of a physiological sensing device 10, in accordance with one or more embodiments of the present disclosure. The device 10 includes a probe 12 that, in the illustrated embodiment, is electrically coupled to a handheld computing device 14 by a cable 17. The cable 17 includes a connector 18 that detachably connects the probe 12 to the computing device 14. The handheld computing device 14 may be any portable computing device having a display, such as a tablet computer, a smartphone, or the like. In some embodiments, the probe 12 need not be electrically coupled to the handheld computing device 14, but may operate independently of the handheld computing device 14, and the probe 12 may communicate with the handheld computing device 14 via a wireless communication channel.

The probe 12 is configured to transmit an ultrasound signal toward a target structure and to receive echo signals returning from the target structure in response to transmission of the ultrasound signal. The probe 12 includes an ultrasound sensor 20 that, in various embodiments, may include an array of transducer elements (e.g., a transducer array) capable of transmitting an ultrasound signal and receiving subsequent echo signals.

The device 10 further includes processing circuitry and driving circuitry. In part, the processing circuitry controls the transmission of the ultrasound signal from the ultrasound sensor 20. The driving circuitry is operatively coupled to the ultrasound sensor 20 for driving the transmission of the ultrasound signal, e.g., in response to a control signal received from the processing circuitry. The driving circuitry and processor circuitry may be included in one or both of the probe 12 and the handheld computing device 14. The device 10 also includes a power supply that provides power to the driving circuitry for transmission of the ultrasound signal, for example, in a pulsed wave or a continuous wave mode of operation.

The ultrasound sensor 20 of the probe 12 may include one or more transmit transducer elements that transmit the ultrasound signal and one or more receive transducer elements that receive echo signals returning from a target structure in response to transmission of the ultrasound signal. In some embodiments, some or all of the transducer elements of the ultrasound sensor 20 may act as transmit transducer elements during a first period of time and as receive transducer elements during a second period of time that is different than the first period of time (i.e., the same transducer elements may be usable to transmit the ultrasound signal and to receive echo signals at different times).

The computing device 14 shown in FIG. 1 includes a display screen 22 and a user interface 24. The display screen 22 may be a display incorporating any type of display technology including, but not limited to, LCD or LED display technology. The display screen 22 is used to display one or more images generated from echo data obtained from the echo signals received in response to transmission of an ultrasound signal, and in some embodiments, the display screen 22 may be used to display color flow image information, for example, as may be provided in a Color Doppler imaging (CDI) mode. Moreover, in some embodiments, the display screen 22 may be used to display audio waveforms, such as waveforms representative of an acquired or conditioned auscultation signal.

In some embodiments, the display screen 22 may be a touch screen capable of receiving input from a user that touches the screen. In such embodiments, the user interface 24 may include a portion or the entire display screen 22, which is capable of receiving user input via touch. In some embodiments, the user interface 24 may include one or more buttons, knobs, switches, and the like, capable of receiving input from a user of the ultrasound device 10. In some embodiments, the user interface 24 may include a microphone 30 capable of receiving audible input, such as voice commands.

The computing device 14 may further include one or more audio speakers 28 that may be used to output acquired or conditioned auscultation signals, or audible representations of echo signals, blood flow during Doppler ultrasound imaging, or other features derived from operation of the device 10.

The probe 12 includes a housing, which forms an external portion of the probe 12. The housing includes a sensor portion located near a distal end of the housing, and a handle portion located between a proximal end and the distal end of the housing. The handle portion is proximally located with respect to the sensor portion.

The handle portion is a portion of the housing that is gripped by a user to hold, control, and manipulate the probe 12 during use. The handle portion may include gripping features, such as one or more detents, and in some embodiments, the handle portion may have a same general shape as portions of the housing that are distal to, or proximal to, the handle portion.

The housing surrounds internal electronic components and/or circuitry of the probe 12, including, for example, electronics such as driving circuitry, processing circuitry, oscillators, beamforming circuitry, filtering circuitry, and the like. The housing may be formed to surround or at least partially surround externally located portions of the probe 12, such as a sensing surface. The housing may be a sealed housing, such that moisture, liquid or other fluids are prevented from entering the housing. The housing may be formed of any suitable materials, and in some embodiments, the housing is formed of a plastic material. The housing may be formed of a single piece (e.g., a single material that is molded surrounding the internal components) or may be formed of two or more pieces (e.g., upper and lower halves) which are bonded or otherwise attached to one another.

In some embodiments, the probe 12 includes a motion sensor. The motion sensor is operable to sense a motion of the probe 12. The motion sensor is included in or on the probe 12 and may include, for example, one or more accelerometers, magnetometers, or gyroscopes for sensing motion of the probe 12. For example, the motion sensor may be or include any of a piezoelectric, piezoresistive, or capacitive accelerometer capable of sensing motion of the probe 12. In some embodiments, the motion sensor is a tri-axial motion sensor capable of sensing motion about any of three axes. In some embodiments, more than one motion sensor 16 is included in or on the probe 12. In some embodiments, the motion sensor includes at least one accelerometer and at least one gyroscope.

The motion sensor may be housed at least partially within the housing of the probe 12. In some embodiments, the motion sensor is positioned at or near the sensing surface of the probe 12. In some embodiments, the sensing surface is a surface which is operably brought into contact with a patient during an examination, such as for ultrasound imaging or auscultation sensing. The ultrasound sensor 20 and one or more auscultation sensors are positioned on, at, or near the sensing surface.

In some embodiments, the transducer array of the ultrasound sensor 20 is a one-dimensional (1D) array or a two-dimensional (2D) array of transducer elements. The transducer array may include piezoelectric ceramics, such as lead zirconate titanate (PZT), or may be based on microelectromechanical systems (MEMS). For example, in various embodiments, the ultrasound sensor 20 may include piezoelectric micromachined ultrasonic transducers (PMUT), which are microelectromechanical systems (MEMS)-based piezoelectric ultrasonic transducers, or the ultrasound sensor 20 may include capacitive micromachined ultrasound transducers (CMUT) in which the energy transduction is provided due to a change in capacitance.

The ultrasound sensor 20 may further include an ultrasound focusing lens, which may be positioned over the transducer array, and which may form a part of the sensing surface. The focusing lens may be any lens operable to focus a transmitted ultrasound beam from the transducer array toward a patient and/or to focus a reflected ultrasound beam from the patient to the transducer array. The ultrasound focusing lens may have a curved surface shape in some embodiments. The ultrasound focusing lens may have different shapes, depending on a desired application, e.g., a desired operating frequency, or the like. The ultrasound focusing lens may be formed of any suitable material, and in some embodiments, the ultrasound focusing lens is formed of a room-temperature-vulcanizing (RTV) rubber material.

In some embodiments, first and second membranes are positioned adjacent to opposite sides of the ultrasound sensor 20 and form a part of the sensing surface. The membranes may be formed of any suitable material, and in some embodiments, the membranes are formed of a room-temperature-vulcanizing (RTV) rubber material. In some embodiments, the membranes are formed of a same material as the ultrasound focusing lens.

Figure 2:
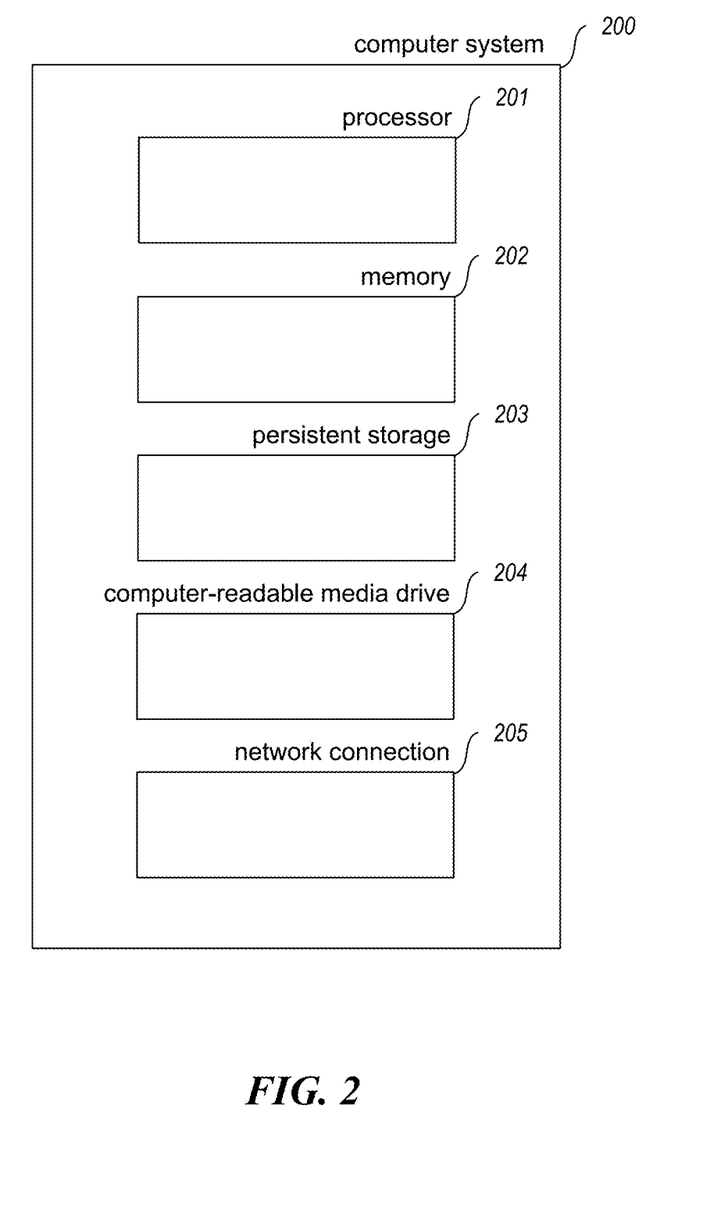
FIG. 2 is a block diagram showing some of the components typically incorporated in at least some of the computer systems and other devices on which the facility operates.

FIG. 2 is a block diagram showing some of the components typically incorporated in at least some of the computer systems and other devices on which the facility operates. In various embodiments, these computer systems and other devices 200 can include server computer systems, cloud computing platforms or virtual machines in other configurations, desktop computer systems, laptop computer systems, netbooks, mobile phones, personal digital assistants, televisions, cameras, automobile computers, electronic media players, physiological sensing devices, and/or their associated display devices, etc. In various embodiments, the computer systems and devices include zero or more of each of the following: a processor 201 for executing computer programs and/or training or applying machine learning models, such as a CPU, GPU, TPU, NNP, FPGA, or ASIC; a computer memory 202 for storing programs and data while they are being used, including the facility and associated data, an operating system including a kernel, and device drivers; a persistent storage device 203, such as a hard drive or flash drive for persistently storing programs and data; a computer-readable media drive 204, such as a floppy, CD-ROM, or DVD drive, for reading programs and data stored on a computer-readable medium; and a network connection 205 for connecting the computer system to other computer systems to send and/or receive data, such as via the Internet or another network and its networking hardware, such as switches, routers, repeaters, electrical cables and optical fibers, light emitters and receivers, radio transmitters and receivers, and the like. While computer systems configured as described above are typically used to support the operation of the facility, those skilled in the art will appreciate that the facility may be implemented using devices of various types and configurations, and having various components.

Figure 3:
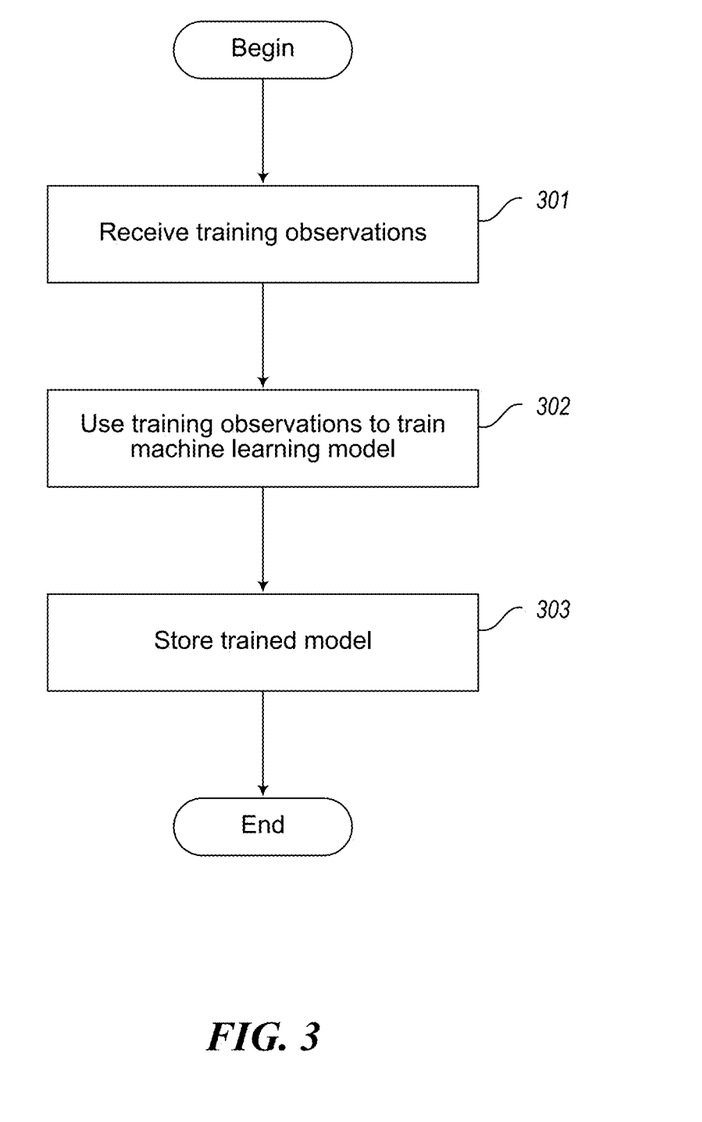
FIG. 3 is a flow diagram showing a process performed by a facility in some embodiments in order to train a machine learning model used by the facility.

FIG. 3 is a flow diagram showing a process performed by a facility in some embodiments in order to train a machine learning model used by the facility. In act 301, the facility receives training observations. In act 302, the facility uses the training observations received in act 301 to train the machine learning model. In act 303, the facility stores the model trained in act 302. After act 303, this process concludes.

Those skilled in the art will appreciate that the acts shown in FIG. 3 and in each of the flow diagrams discussed below may be altered in a variety of ways. For example, the order of the acts may be rearranged; some acts may be performed in parallel; shown acts may be omitted, or other acts may be included; a shown act may be divided into subacts, or multiple shown acts may be combined into a single act, etc.

Figure 4:
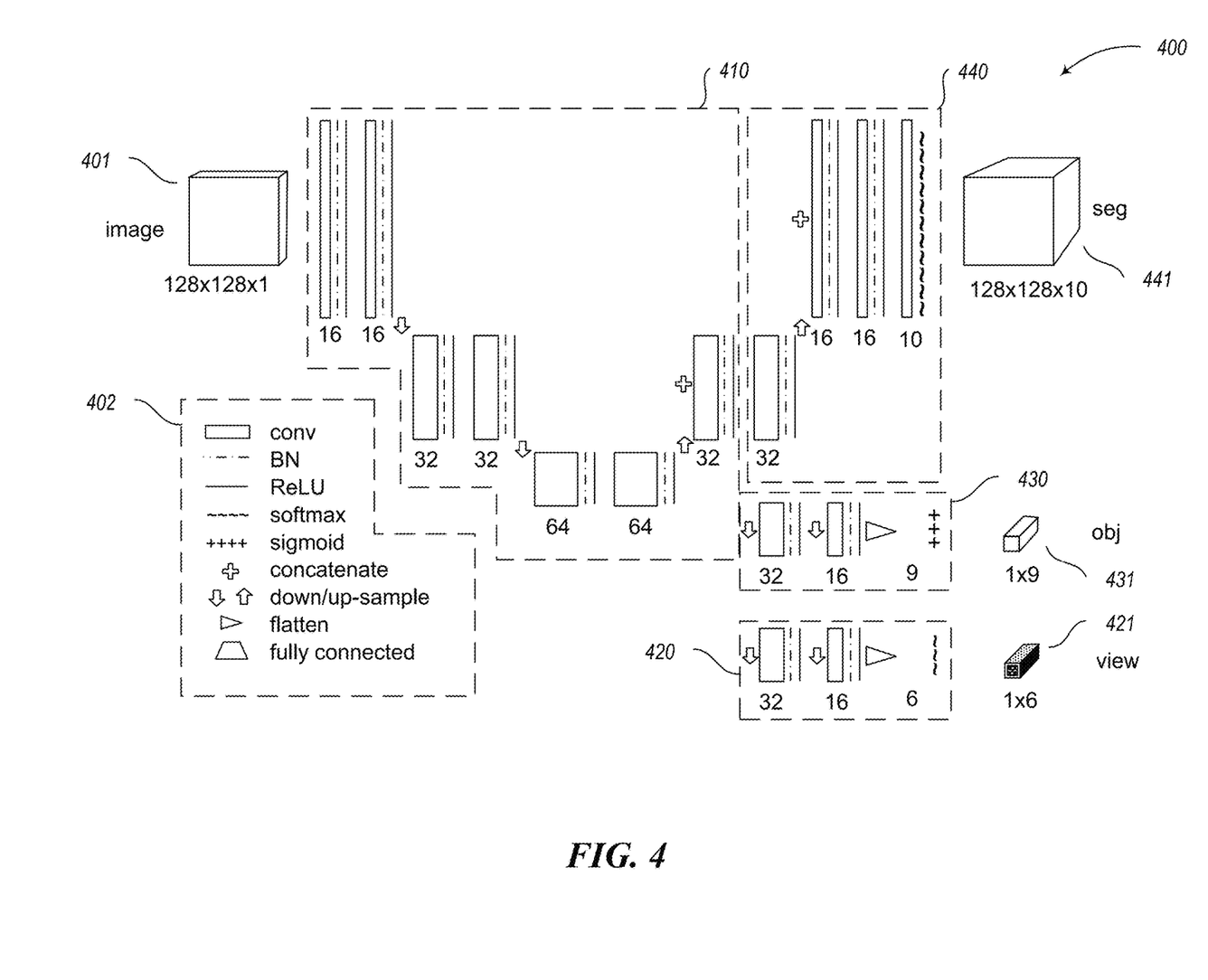
FIG. 4 is a model architecture drawing showing details of the design of the machine learning model used by the facility.

FIG. 4 is a model architecture drawing showing details of the design of the machine learning model used by the facility in some embodiments. As shown in the architecture 400, on the basis of an image 401, such as patient ultrasound image, the facility predicts three characteristics of the image: a view probability vector 421 that indicates, for each of a number of possible views, the likelihood that the image was captured from that view; an object probability vector 431 that indicates, for each of a number of possible objects, the likelihood that the image visualizes the object; and a set or cube 441 of segmentation masks that, for each pixel of the image, for each of the possible objects, indicate the probability that the pixel is a part of a visualization of the object. The model is shown as a deep learning neural network, made up of a shared section 410, a view probability branch 420 dedicated to predicting the view probability vector characteristic; an object probability branch 430 dedicated to predicting the object probability vector characteristic; and a segmentation branch 440 dedicated to predicting the segmentation mask cube. Legend 402 describes the symbology used in diagramming the network architecture. In particular, "conv" stands for convolutional layers, "BN" stands for batch normalization layers, and "ReLU" rectified linear unit. The number under each layer represents either number of channels or dimensionality. All convolution layers are of 3×3 kernel. In a variety of embodiments, the facility uses a variety of other neural network or other machine learning model architectures to predict the three image characteristics used by the facility.

Figure 5:
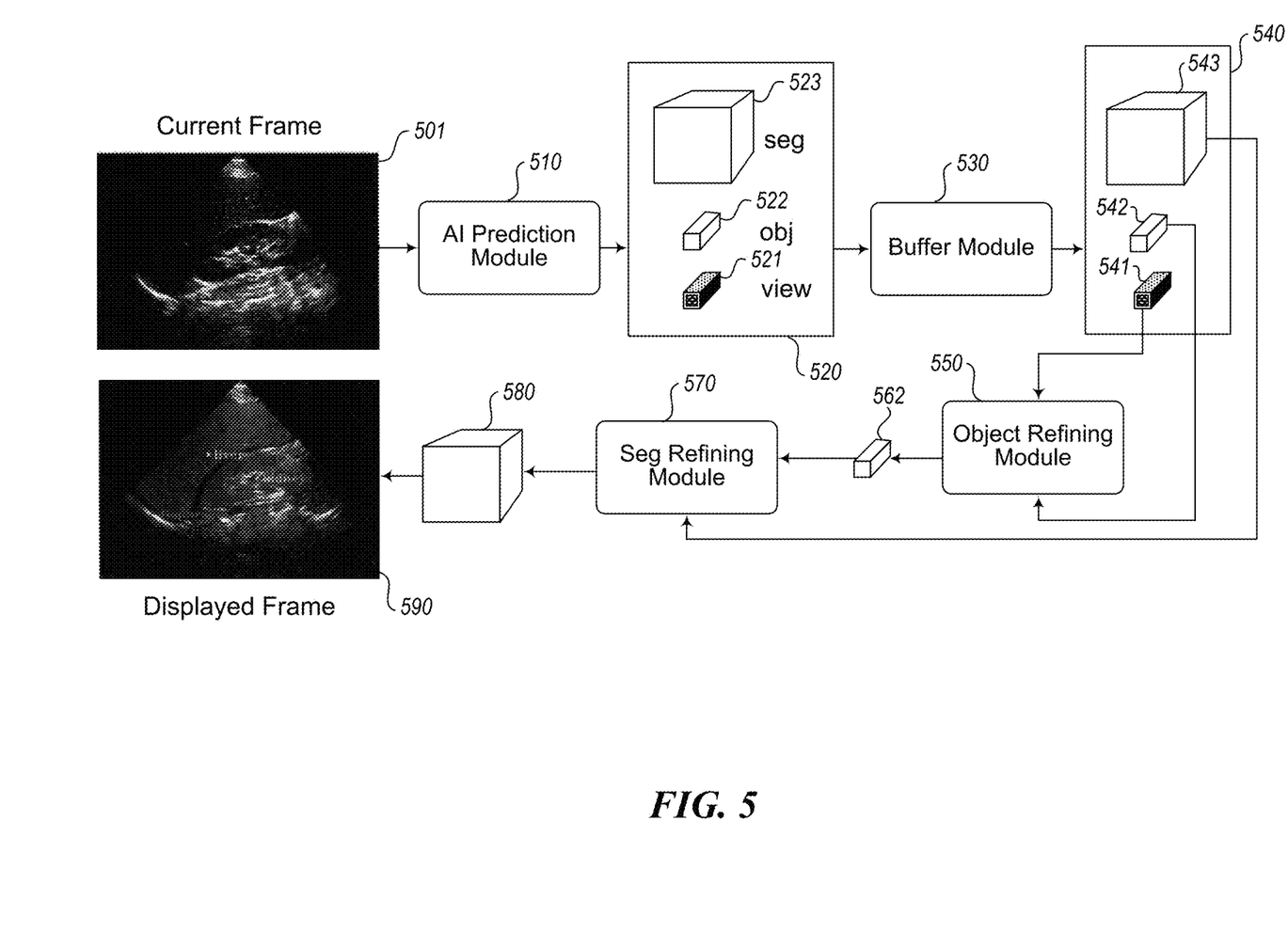
FIG. 5 is a data flow diagram showing the data flow used by the facility.

FIG. 5 is a data flow diagram showing the data flow used by the facility in some embodiments to identify the anatomical objects in a patient video frame, and use this information to augment the frame for display. The data flow begins with a current patient video frame 501 received from imaging hardware.

Figure 6:
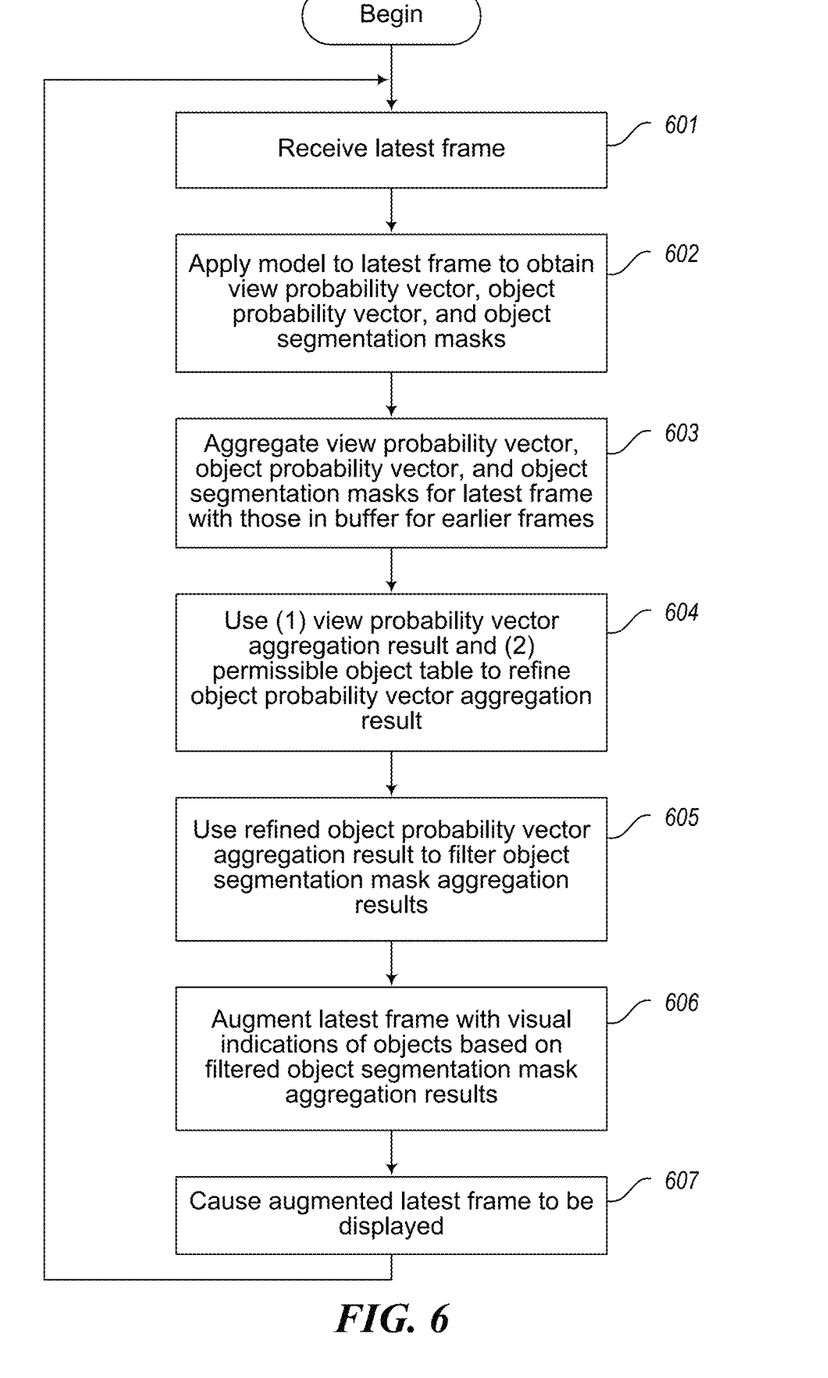
FIG. 6 is a flow diagram showing a process performed by the facility.

FIG. 6 is a flow diagram showing a process performed by the facility in order to effect the data flow shown in FIG. 5 to identify anatomical objects in patient video and use this information to augment frames of the video. In act 601, the facility receives the latest frame from the imaging hardware.

Figure 7:
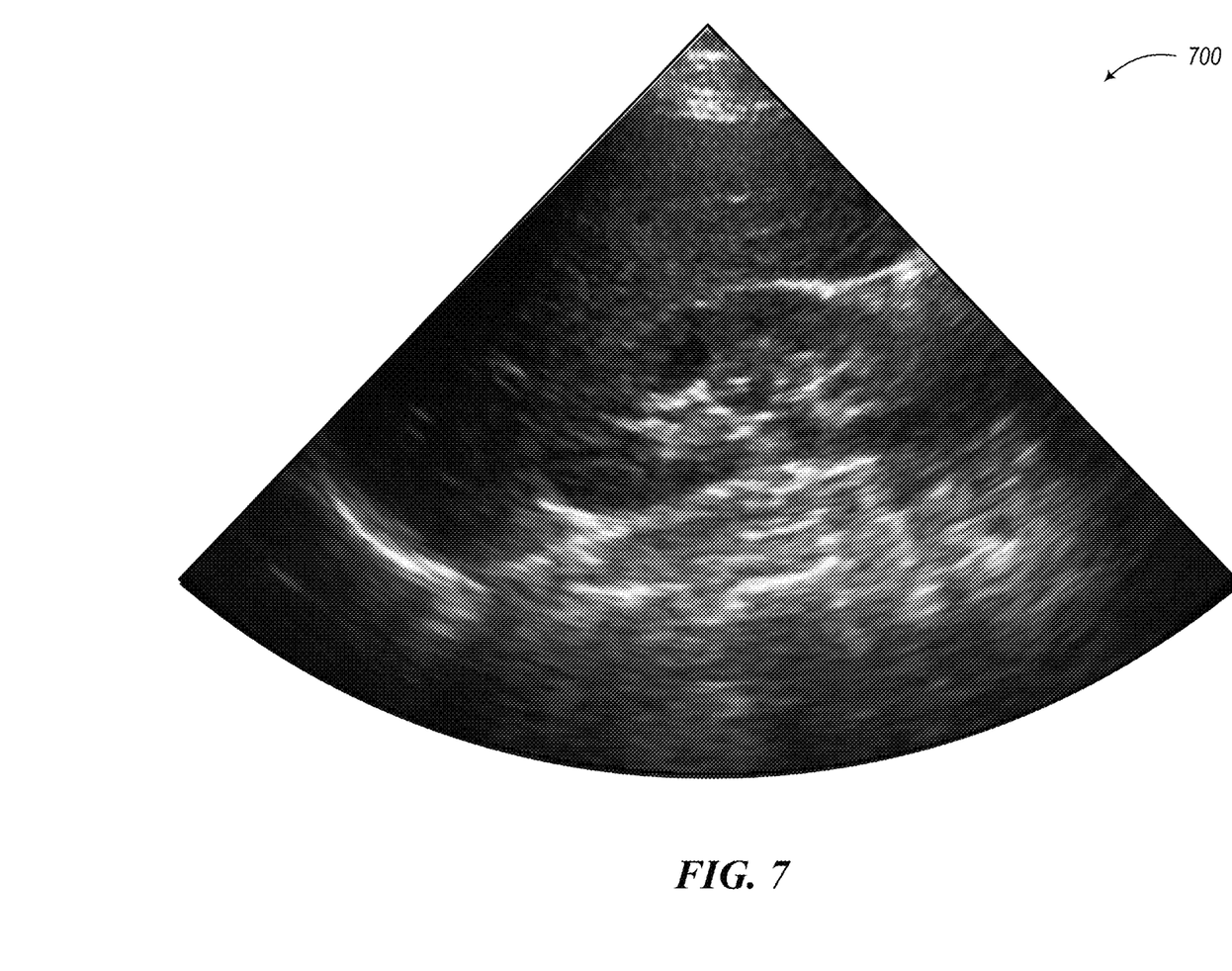
FIG. 7 is an image diagram showing a sample patient video frame received by the facility.

FIG. 7 is an image diagram showing a sample patient video frame received by the facility. In particular, the frame 700 is a frame of a patient ultrasound video.

Returning to FIG. 6, in act 602, in an AI prediction module 510, the facility applies the machine learning model trained by the facility to the latest frame 501 received in act 601 to obtain the following characteristics of the image constituting the frame: a view probability vector 521, an object probability vector 522, and a segmentation mask cube 523.

In act 603, in a buffer module 530, the facility aggregates the three image characteristics 520 produced in act 602 with earlier sets of image characteristics maintained in the buffer for earlier frames, such as the 4, 9, 19, or 29 previous frames. In various embodiments, the facility uses a variety of aggregation functions, including mean, median, mode, minimum, maximum, etc. Act 603 produces a set 540 of aggregated image characteristics.

The operation of the facility is described with respect to a particular example based upon current frame 501, shown with greater magnification as frame 700 in FIG. 7. Table 1 below shows contents of the aggregated view probability vector 541 determined by the facility for the current frame.

TABLE 1

| View | Probability |
|---|---|
| right-upper quadrant | 0.7 |
| left-upper quadrant | 0.2 |
| subcostal | 0 |
| inferior vena cava | 0 |
| suprapubic | 0 |
| others | 0.1 |

For example, this view probability vector indicates a 20% likelihood that the current frame and those who preceded it whose information is included in the aggregate were captured from the left-upper quadrant view.

Contents of the aggregated object probability vector 542 for the example are shown below in Table 2.

TABLE 2

| Object | Probability |
|---|---|
| liver | 0.9 |
| kidney | 0.8 |
| diaphragm | 0.8 |
| spleen | 0.5 |
| heart | 0 |
| inferior vena cava | 0 |
| bladder | 0.05 |
| uterus | 0 |
| prostate | 0 |

For example, the contents of this object probability vector indicate a 50% likelihood that the spleen object is visualized in the sample image and those that precede it. In the example, a segmentation mask cube 543 is also produced that corresponds to the current frame and those that preceded it; for compactness, the contents of the segmentation of the mask cube are not shown.

In act 604, in an object refining module 550, the facility uses the view probably vector aggregation result 541 and a permissible object table to refine the object probability vector aggregation result 542, thus producing a refined object probability vector aggregation result 562.

Figure 8:
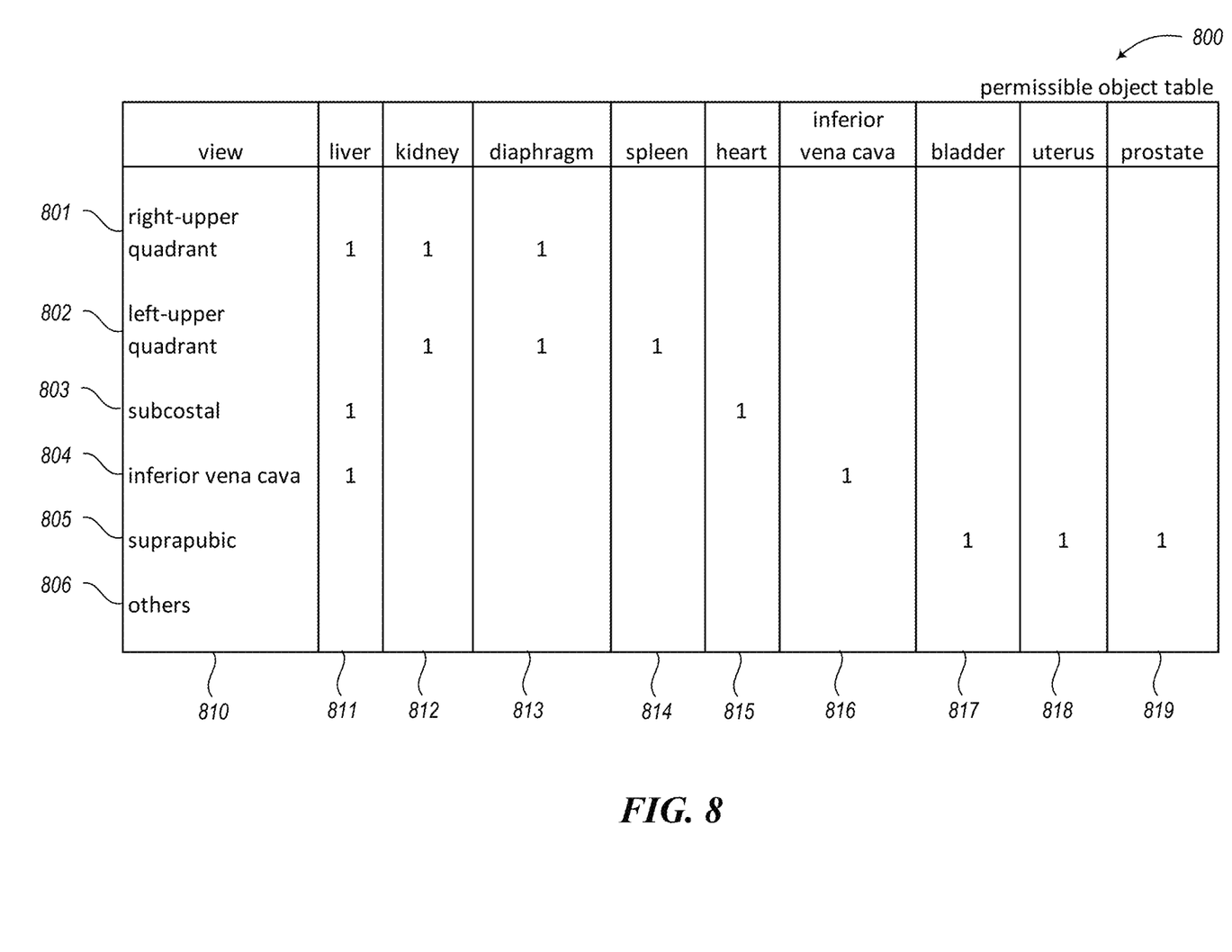
FIG. 8 is a table diagram showing sample contents of a permissible object table.

FIG. 8 is a table diagram showing sample contents of a permissible object table used by the facility in some embodiments. In particular, the permissible object table 800 shows, for each of a number of views 801-806, whether it is permissible for the view to visualize each of a number of organs or other objects 811-819. For example, the intersection of column 811 with rows 801 and 802 shows that the liver is permitted to be visualized in the right-upper quadrant view, but not the left-upper quadrant view.

While FIG. 8 and each of the table diagrams discussed below show a table whose contents and organization are designed to make them more comprehensible by a human reader, those skilled in the art will appreciate that actual data structures used by the facility to store this information may differ from the table shown, in that they, for example, may be organized in a different manner; may contain more or less information than shown; may be compressed, encrypted, and/or indexed; may contain a much larger number of rows than shown, etc.

In performing step 604, the facility refines each value of the object probability vector aggregation result shown in Table 2 as follows: first, the facility uses the permissible object table to determine, for the object to which the value of the vector corresponds, which views are permitted to visualize the object. Using the kidney object as an example, column 812 of the permissible object table shows that the kidney is permitted to be visualized in only two views: the right-upper quadrant view and the left-upper quadrant view. In response, the facility sums the view probabilities in the view probability vector aggregation result for these objects. With respect to the kidney object, the facility sums the view probability for the right-upper quadrant view, 0.7, with the view probability for the left-upper quadrant view, 0.2, to obtain a sum of 0.9. The facility then multiplies this sum of selected view probabilities by the object probability for the object. In the example of the kidney object, the facility multiplies the sum 0.9 by the initial object probability of 0.8 to obtain a refined object probability for the kidney of 0.72. The facility performs this process with respect to each of the objects in order to obtain refined object probability vector aggregation result 562, the contents of which in the example are shown below in Table 3.

TABLE 3

| Object | Refined Probability | Select Segmentation Mask |
|---|---|---|
| liver | 0.63 | yes |
| kidney | 0.72 | yes |
| diaphragm | 0.72 | yes |
| spleen | 0.1 | |
| heart | 0 | |
| inferior vena cava | 0 | |
| bladder | 0 | |
| uterus | 0 | |
| prostate | 0 | |

In act 605, in a segment refining module 570, the facility uses the refined object probability vector aggregation result 562 obtained in act 604 to filter the masks included in the object segmentation mask aggregation result 543. In particular, the facility applies a minimum probability, such as 60%, to the value for each object in the refined object probability vector aggregation result. In terms of the example, applying the minimum probability of 0.6, the facility selects the segmentation masks for only the liver, whose refined probability is 0.63, and the kidney and diaphragm, whose refined probabilities are both 0.72. Thus, the facility includes the segmentation masks in cube 543 for the liver, kidney, and diaphragm objects in filtered segmentation mask cube 580. In act 606, the facility augments the current frame 501 with visual indications of identified objects that are based on the filtered object segmentation mask aggregation results 580 produced in act 605 to obtain displayed frame 590.

Figure 9:
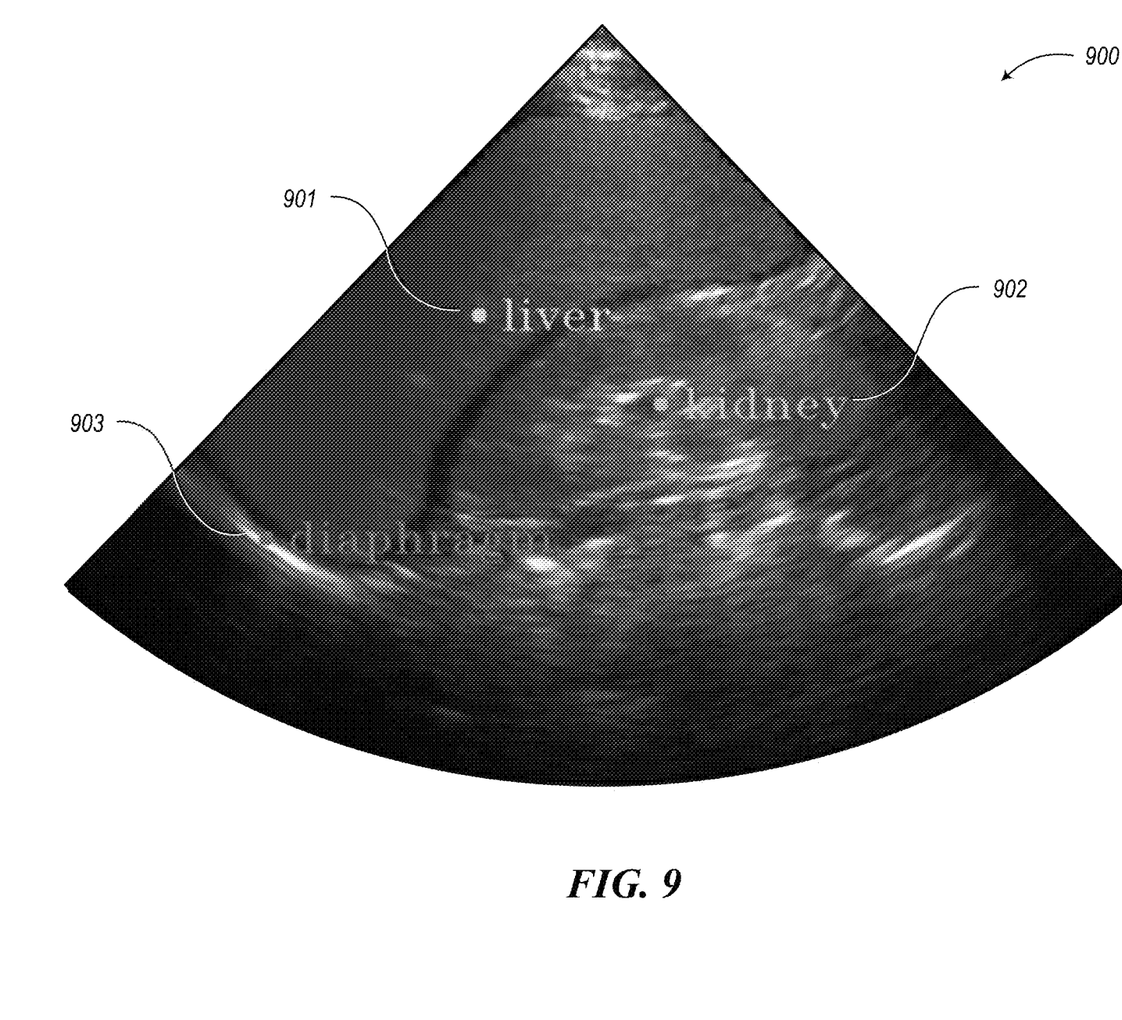
FIG. 9 is a display diagram showing a version of the sample patient video frame that the facility has augmented to visually indicate objects identified as visualized in the current frame.

FIG. 9 is a display diagram showing a version of the sample patient video frame that the facility has augmented to visually indicate objects identified as visualized in the current frame. It can be seen that augmented frame 900 includes a visual indication 901 of the liver object, and indication 902 of the kidney object, and an indication 903 of the diaphragm object. In various embodiments, these visual indications are of varying character. For example, in various embodiments, these are unfilled shapes; filled shapes whose brightness and intensity vary based upon the probability in the corresponding segmentation mask and/or visual data in the original image; filled shapes of a constant intensity; etc.

Returning to FIG. 6, in act 607, the facility causes the augmented latest frame 590 produced in act 606 to be displayed, such as on the display device physically connected to the imaging sensor, a local display device wirelessly connected to the imaging sensor; a remote display device, etc. After act 607, the facility continues in act 601 to process the next frame of the patient video.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A system, comprising:
an ultrasound sensing device; and
a computing device, the computing device comprising:
a communication interface configured to directly receive ultrasound echo data sensed by the ultrasound sensing device from a person, the received ultrasound echo data comprising an ultrasound video comprising a sequence of frames, each frame comprised of pixels;
a memory configured to:
store one or more neural networks trained to, for an ultrasound video frame comprised of pixels:
for each respective ultrasound view of a plurality of ultrasound views, assign a probability that the frame was captured from the respective ultrasound view,
for each respective anatomical object of a plurality of anatomical objects:
assign a probability that the frame visualizes the respective anatomical object, and
for each of the pixels of the frame, assign a probability that the anatomical object is visualized in the pixel;
store, for each of the plurality of anatomical objects, a list of views in which the anatomical object is permitted; and
store an object probability threshold and a pixel probability threshold;
a processor configured to:
for each respective frame of the sequence of frames:
apply the one or more trained neural networks to the respective frame to:
for each respective view of the plurality of views, assign a probability that the frame was captured from the view,
for each respective anatomical object of the plurality of anatomical objects:
assign a probability that the respective frame visualizes the anatomical object, and
for each respective pixel of the pixels of the frame, assign a probability that the anatomical object is visualized in the respective pixel;
identify anatomical objects visualized in the respective frame by, for each respective anatomical object of the plurality of anatomical objects:
accessing the stored list of views in which the anatomical object is permitted,
summing the probabilities assigned to the views on the accessed list,
multiplying the sum by the probability assigned to the respective anatomical object to obtain a refined probability for the respective anatomical object, and
where the refined probability for the respective anatomical object exceeds the stored object probability threshold, augmenting the respective frame to indicate that the respective anatomical object is visualized by the frame in the pixels whose pixel probabilities for the anatomical object exceed the pixel probability threshold; and
a display device configured to:
for each respective frame of the sequence of frames:
display the respective frame as augmented.

2. The system of claim 1 wherein the ultrasound sensing device and computing device are physically connected.

3. The system of claim 1 wherein the ultrasound sensing device comprises a transducer.

4. The system of claim 1 wherein the processor is further configured to, for each frame, before the identification, aggregate into the probabilities assigned for the frame probabilities assigned for one or more frames preceding the frame in the sequence.

5. The system of claim 1 wherein each of the plurality of anatomical objects is an organ.

6. The system of claim 1 wherein each of the plurality of anatomical objects is a sub-organ structure.

7. One or more instances of computer-readable media collectively having contents configured to cause a computing system to perform a method, the method comprising:
accessing a medical imaging image;
accessing a first machine learning model trained to predict for an image a view probability vector that, for each of a plurality of views, assigns a probability that the image was captured from the view;
applying the first machine learning model to the accessed image to predict a view probability vector for the accessed image;
accessing a second machine learning model trained to predict for an image an object probability vector that, for each of a plurality of anatomical objects, assigns a probability that the anatomical object is visualized by the image;

applying the second machine learning model to the accessed image to predict an object probability vector for the accessed image;

for each respective anatomical object of the plurality of anatomical objects:

accessing a stored list of views in which the respective anatomical object is permitted, multiplying the predicted probability that the respective anatomical object is visualized by the accessed image by the sum of the predicted probabilities that the accessed image was captured from views in which the respective anatomical object is permitted to obtain a refined probability that the respective anatomical object is visualized by the accessed image; and where the refined probability that the respective anatomical object is visualized by the accessed image exceeds a probability threshold, determining that the object is visualized by the accessed image.

8. The one or more instances of computer-readable media of claim 7, the method further comprising:

storing in connection with the accessed image an indication of the anatomical objects determined to be visualized by the accessed image.

9. The one or more instances of computer-readable media of claim 7, the method further comprising:

accessing a third machine learning model trained to predict for an image, for each respective anatomical object of the plurality of anatomical objects, a segmentation mask identifying pixels of the image in which the respective anatomical object is visualized;

applying the third machine learning model to the accessed image to predict a segmentation mask for the accessed image for each of the plurality of anatomical objects; and using the segmentation masks for the anatomical objects determined to be visualized by the accessed image to augment the accessed image to indicate locations of the anatomical objects determined to be visualized by the accessed image.

10. The one or more instances of computer-readable media of claim 9 wherein the first, second, and third machine learning models share a common series of neural network layers.

11. The one or more instances of computer-readable media of claim 9, the method further comprising:

storing the augmented image.

12. The one or more instances of computer-readable media of claim 9, the method further comprising:

causing the augmented image to be displayed.

13. The one or more instances of computer-readable media of claim 9, the method further comprising:

causing a list of the objects determined to be visualized by the accessed image to be displayed.

14. The one or more instances of computer-readable media of claim 7, the method further comprising:

training the first machine learning model; and training the second machine learning model.

15. The one or more instances of computer-readable media of claim 7 wherein the accessed image is an ultrasound image.

16. The one or more instances of computer-readable media of claim 7 wherein the contents are configured to cause the computing system to perform the method for each of a sequence of accessed images captured from the same patient.

17. A method in a computing system for training a machine learning model, the method comprising:

accessing a body of annotated ultrasound image training observations;

using at least a portion of the body of annotated training observations to train a first machine learning model to predict, based on an ultrasound image, for each respective view of a plurality of respective views, a probability that the image was captured from the respective view;

using at least a portion of the body of annotated training observations to train a second machine learning model to predict, based on an ultrasound image, for each respective anatomical object of a plurality of anatomical objects, a probability that the respective anatomical object is visualized by the image;

persistently storing the trained first and second machine learning models; and persistently storing, for each respective view of a plurality of views represented by ultrasound images, indications of one or more anatomical objects that are expected to be visualizable in ultrasound images captured from the respective view, wherein:

a production ultrasound image can be subjected to the first machine learning model to predict, for each respective view of the plurality of views, a probability that the production ultrasound image was captured from the respective view, the production ultrasound image can be subjected to the second machine learning model to predict, for each respective anatomical object of the plurality of objects, a probability that the respective object is visualized by the product ultrasound image, and for each respective anatomical object of the plurality of anatomical objects, the probability that the anatomical object is visualized by the production ultrasound image predicted by subjecting the production ultrasound image to the second machine learning model can be refined by multiplying it by the sum of the probabilities predicted by subjecting the production ultrasound image to the first machine learning model for the views in which the anatomical object is indicated to be expected to be visualizable.

18. The method of claim 17 wherein a portion of the second machine learning model is shared with the first machine learning model.

* * * * *

UNITED STATES PATENT AND TRADEMARK OFFICE
CERTIFICATE OF CORRECTION

| | | |
|---|---|---|
| PATENT NO. | : 11,636,593 B2 | Page 1 of 1 |
| APPLICATION NO. | : 17/091263 | |
| DATED | : April 25, 2023 | |
| INVENTOR(S) | : Babajide Ayinde et al. | |

It is certified that error appears in the above-identified patent and that said Letters Patent is hereby corrected as shown below:

In the Claims

Column 9, Claim 1, Line 62:
"for each of the pixels of the frame,"
Should read:
--for each respective pixel of the pixels of the frame,--.

Column 9, Claim 1, Line 64:
"in the pixel;"
Should read:
--in the respective pixel;--.

Column 11, Claim 7, Lines 18-19:
"that the object is visualized"
Should read:
--that the respective anatomical object is visualized--.

Column 12, Claim 17, Line 41:
"the plurality of objects,"
Should read:
--the plurality of anatomical objects,--.

Column 12, Claim 17, Line 43:
"the product ultrasound image, and"
Should read:
--the production ultrasound image, and--.

Signed and Sealed this
Twenty-fifth Day of February, 2025

Coke Morgan Stewart
*Acting Director of the United States Patent and Trademark Office*